United States Patent
Cotton et al.

(10) Patent No.: US 12,415,027 B2
(45) Date of Patent: Sep. 16, 2025

(54) RELATING TO APPARATUS NEGATIVE PRESSURE WOUND THERAPY

(71) Applicant: BRIGHTWAKE LIMITED, Kirkby in Ashfield (GB)

(72) Inventors: Stephen Cotton, Kirkby in Ashfield (GB); Matthew Tasker, Kirkby in Ashfield (GB)

(73) Assignee: BRIGHTWAKE LIMITED, Kirkby in Ashfield (GB)

( * ) Notice: Subject to any disclaimer, the term of this patent is extended or adjusted under 35 U.S.C. 154(b) by 169 days.

(21) Appl. No.: 18/505,461

(22) Filed: Nov. 9, 2023

(65) Prior Publication Data
US 2024/0075199 A1    Mar. 7, 2024

Related U.S. Application Data

(63) Continuation of application No. 16/491,855, filed as application No. PCT/GB2018/050409 on Feb. 15, 2018, now Pat. No. 11,878,108.

(30) Foreign Application Priority Data

Mar. 9, 2017    (GB) ..................... 1703806

(51) Int. Cl.
    *A61M 1/00*        (2006.01)
    *A61F 13/0203*     (2024.01)
    (Continued)

(52) U.S. Cl.
    CPC ............ *A61M 1/96* (2021.05); *A61F 13/0209* (2013.01); *A61F 13/0213* (2013.01);
    (Continued)

(58) Field of Classification Search
    CPC ............ A61M 1/96; A61M 1/73; A61M 1/74; A61M 1/985; A61M 39/24;
    (Continued)

(56) References Cited

U.S. PATENT DOCUMENTS

| 4,650,477 A | 3/1987 | Johnson |
| 2011/0077605 A1 | 3/2011 | Karpowicz et al. |

(Continued)

FOREIGN PATENT DOCUMENTS

| EP | 0111087 A1 | 10/1983 |
| WO | 2012/038727 A2 | 3/2012 |

(Continued)

OTHER PUBLICATIONS

International Search Report and Written Opinion for corresponding Application No. PCT/GB2018/050409 (mailed May 2, 2018).

(Continued)

*Primary Examiner* — Jessica Arble
*Assistant Examiner* — Hans Kaliher
(74) *Attorney, Agent, or Firm* — Troutman Pepper Locke LLP

(57) ABSTRACT

An apparatus (1) for negative pressure wound therapy comprises a source of reduced pressure (10) and first (22*a*) and second (26*a*) chambers, the first chamber being in fluid communication with the source of reduced pressure such that a negative pressure may be generated in the first chamber, the negative pressure being prevented from exceeding a predetermined value by way of a pressure release means (30), and the second chamber comprising means (28) for establishing a fluid connection with a wound. A valve (24) between the first and second chambers permits the negative pressure in the second chamber to increase in response to an increase in the negative pressure in the first chamber and prevents the negative pressure in the second chamber from dropping in response to a drop in the negative pressure in the first chamber.

21 Claims, 3 Drawing Sheets

(51) Int. Cl.
    *A61F 13/0206*     (2024.01)
    *A61F 13/05*     (2024.01)
    *A61M 39/24*     (2006.01)

(52) U.S. Cl.
    CPC ............... *A61F 13/05* (2024.01); *A61M 1/73* (2021.05); *A61M 1/74* (2021.05); *A61M 1/985* (2021.05); *A61M 39/24* (2013.01); *A61M 2205/02* (2013.01)

(58) Field of Classification Search
    CPC ............ A61M 2205/02; A61F 13/0209; A61F 13/0213; A61F 13/05
    See application file for complete search history.

(56) References Cited

U.S. PATENT DOCUMENTS

| | | |
|---|---|---|
| 2013/0131616 A1 | 5/2013 | Locke |
| 2013/0144227 A1 | 6/2013 | Locke et al. |
| 2013/0144235 A1 | 6/2013 | Augustine et al. |
| 2013/0296816 A1 | 11/2013 | Greener |
| 2013/0317462 A1 | 11/2013 | Yao et al. |
| 2013/0331823 A1 | 12/2013 | Askem et al. |
| 2015/0018784 A1 | 1/2015 | Coulthard et al. |
| 2016/0144084 A1 | 5/2016 | Collinson et al. |
| 2017/0028113 A1 | 2/2017 | Shuler et al. |
| 2017/0368239 A1 | 12/2017 | Askem |
| 2018/0311419 A1* | 11/2018 | Locke .................. A61F 13/05 |
| 2018/0345001 A1 | 12/2018 | Heaton et al. |

FOREIGN PATENT DOCUMENTS

| | | |
|---|---|---|
| WO | 2012/166428 A1 | 12/2012 |
| WO | 2022/049363 A1 | 3/2022 |

OTHER PUBLICATIONS

Great Britain Search Report for corresponding Application No. GB1703806.8 (mailed Jul. 19, 2017).
Screen shot of Datasheets Website including Koge Product Sheets dated Oct. 23, 2011, https://www.datasheets.com/zh-tw/part-details/kpv08a-3a-koge-micro-tech-co---ltd-46302511 #datasheet (2011).
Web Capture of Datasheet Website including Koge Product Sheets dated Oct. 23, 2011, https://www.datasheets.com/zh-tw/part-details/kpv08a-3a-koge-micro-tech-co---ltd-46302511 #datasheet (Year: 2011).
Koge KPV08-3A data sheet; https://koge-europe.com/en/produkte/kpv08a-3a/; Accessed Mar. 18, 2021.
Nordson Medical Check Valve data sheet; https://www.nordsonmedical.com/Components-and-Technologies/Fluid-Management-Components/Check-Valves/; Accessed Mar. 18, 2021.
International Search Report and Written Opinion for PCT/GB2023/053306, mailed Mar. 20, 2024.

* cited by examiner

RELATING TO APPARATUS NEGATIVE PRESSURE WOUND THERAPY

This application is a continuation of U.S. patent application Ser. No. 16/491,855, filed Sep. 6, 2019, which is a national stage application under 35 U.S.C. § 371 of PCT Application No. PCT/GB2018/050409, filed Feb. 15, 2018, which claims the priority benefit of Great Britain Patent Application No. 1703806.8, filed Mar. 9, 2017.

FIELD OF THE INVENTION

This invention relates generally to negative pressure wound therapy (NPWT), and more specifically to an improved apparatus for performing NPWT.

BACKGROUND TO THE INVENTION

Negative pressure wound therapy (NPWT) involves the application of a pressure that is reduced relative to the surroundings (commonly referred to as "negative pressure") to a wound, which causes mechanical contraction of the wound and removal of wound fluid from the wound, thus promoting formation of granulation tissue and accelerating wound healing. The technique is particularly effective in the treatment of slow healing wounds such as chronic leg ulcers and large open wounds. An occlusive dressing is applied to the wound and forms a seal around the wound under which a negative pressure can be established. The occlusive dressing is traversed by a drainage tube, which is connected to a source of negative pressure which enables a source of reduced pressure to be applied to a wound and for wound fluid to be drained from the wound. The negative pressure that is applied to a wound is typically around 100 mmHg, although a negative pressure in the range of 80-120 mmHg is usually tolerated as movement of the patient or direct pressure on the wound can cause the pressure at the wound site to fluctuate. However, it is generally accepted that the application of a negative pressure in excess of 120 mmHg to a wound is undesirable.

Apparatus for NPWT typically includes means for carefully managing the negative pressure that is applied to the wound in order to ensure that it is retained in the desired range of 80-120 mmHg. In particular, the apparatus must prevent the negative pressure that is applied to the wound from dropping below 80 mmHg as a result of leaks in NPWT apparatus, which may occur at the wound site as a result of the occlusive dressing not forming a complete seal around the wound, or via the source of reduced pressure as conventional sources of reduced pressure such as vacuum pumps do not typically have an air tight construction. In addition, the apparatus must also prevent the negative pressure that is applied to the wound from exceeding 120 mmHg as a result of excessive activation of the source of reduced pressure.

Accordingly, apparatus for NPWT includes a complex arrangement of conduits and valves for the management of the negative pressure that is applied to the wound. These arrangements include numerous joints between components, all of which are potential sources of leaks and require precision assembly in order to reduce the incidence of leaks, which adds significantly to the cost of manufacturing NPWT apparatus. In addition, many NPWT systems include complex valves such as electronic valves that are expensive and prone to failure.

There is therefore a need for an apparatus for NPWT that comprises a robust and simple means of controlling the negative pressure that is applied to a wound, does not require a complex arrangement of conduits and valves and does not require precision assembly.

There has now been devised an apparatus for negative pressure wound therapy that overcomes or substantially mitigates the above mentioned and/or other problems associated with the prior art.

BRIEF SUMMARY OF THE INVENTION

According to a first aspect of the invention, there is provided an apparatus for negative pressure wound therapy comprising:
  a source of reduced pressure;
  a first chamber in fluid communication with the source of reduced pressure such that the source of reduced pressure is operable to generate a negative pressure in the first chamber;
  a pressure release means that prevents the negative pressure in the first chamber from exceeding a predetermined negative pressure value;
  a second chamber comprising means for establishing fluid communication between the second chamber and a wound;
  a valve located between the first chamber and the second chamber, the valve permitting the negative pressure in the second chamber to increase in response to an increase in the negative pressure in the first chamber, and preventing the negative pressure in the second chamber from dropping in response to a drop in the negative pressure in the first chamber.

The apparatus may be operated by establishing fluid communication between the second chamber and the wound by a suitable means and activating the source of reduced pressure. The operation of the source of reduced pressure generates a negative pressure in the first chamber, which in turn generates a negative pressure in the second chamber and the application of a negative pressure to the wound that is in fluid communication with the second chamber. The pressure release means prevents the negative pressure in the first chamber, and hence the negative pressure in the second chamber and that is applied to the wound, from exceeding a predetermined negative pressure value, regardless of the negative pressure that is generated by the source of reduced pressure. Accordingly, the predetermined negative pressure value is the maximum negative pressure that the apparatus is capable of applying to a wound. The predetermined negative pressure value is preferably 120 mmHg or higher and for example may be 125 mmHg, 130 mmHg, 140 mmHg or 150 mmHg.

The source of reduced pressure may be deactivated in response to the negative pressure that is applied to the wound has reached a desired level. The negative pressure in the first chamber may then drop, for example due to the entry of gas into the first chamber via the source of reduced pressure or the pressure release means. The valve located between the first chamber and the second chamber prevents the negative pressure in the second chamber, and consequently the negative pressure that is applied to the wound, from dropping in response to a drop in the negative pressure in the first chamber. The negative pressure that is applied to the wound may nevertheless drop over time, for example due to the entry of gas into the second chamber or the wound. The source of reduced pressure may be activated in response to the negative pressure that is applied to the wound dropping below a desired level.

The apparatus may further comprise a means for detecting the negative pressure that is applied to the wound. This may comprise means for detecting the negative pressure in the second chamber, and for example may be in fluid communication with the second chamber, as the second chamber and the wound are in fluid communication and hence are at substantially the same negative pressure during operation of the apparatus.

The means for detecting the negative pressure that is applied to the wound may be operably coupled to the source of reduced pressure, for example such that the source of reduced pressure is deactivated in response to the negative pressure that is applied to the wound reaching a desired level and/or the source of reduced pressure is activated in response to the negative pressure that is applied to the wound dropping below a desired level. This arrangement may enable the apparatus to maintain the negative pressure that is applied to the wound at a desired level for as long as the apparatus is in operation without the need for further intervention by an operator.

The desired level of negative pressure that is applied to the wound may be between 75 and 125 mmHg, 80 and 120 mmHg, 90 and 110 mmHg, or about 100 mmHg. The means for detecting the negative pressure that is applied to the wound may be operably coupled to the source of reduced pressure via a programmable computer processor that permits the desired level of negative pressure that is applied to the wound to be varied.

The means for detecting the negative pressure that is applied to the wound may be an electronic pressure sensor such as a piezoresistive electronic pressure sensor. One pressure sensor that is suitable for use with this invention is the 2SMPP-03 MEMS Gauge Pressure Sensor by Omron Corporation.

The source of reduced pressure may be a vacuum pump such as a diaphragm vacuum pump, an electromagnetic vacuum pump or a piezoelectric vacuum pump. The source of reduced pressure may be compact and in particular may have a maximum dimension of less than 100 mm, less than 80 mm, less than 60 mm or less than 40 mm, and may occupy a volume of less than 10 cm$^3$, less than 8 cm$^4$, less than 6 cm$^3$ or less than 4 cm$^3$. The source of reduced pressure is typically the most bulky component of apparatus for negative pressure wound therapy and hence the use of a compact source of reduced pressure is desirable to permit the apparatus to improve the handling and mobility of the apparatus. One example of a vacuum pump that is suitable for use with this invention is the KPV08A-3A Micro Vacuum Pump by Koge Micro Tech Co Ltd.

The source of reduced pressure may be powered by electricity. Accordingly, the apparatus may further comprise a power source for the source of reduced pressure. The power source may comprise one or more batteries, or means for the connection of one or more batteries to the apparatus. In one preferred embodiment, the one or more batteries may be standard batteries such as AA or AAA batteries. The source of reduced pressure preferably has a relatively low power consumption in order to enable it to run for extended periods without the need to replace batteries. In particular, the maximum power consumption of the source of reduced pressure may be less than 5 W, less than 3 W or less than 2 W.

The first and second chambers may be defined by suitable housings. The housings may be in the form of a tube or the like, including a branched tube such as a manifold or T-piece, in which case the first and second chambers correspond to the internal volume of the tube or the like. The housings that define the first and second chambers may be structurally different, but are preferably structurally the same in order to simplify assembly of the apparatus and reduce manufacturing cost.

The housings preferably include openings through which the first and second chambers can form a connection with the other components of the apparatus, including the source of reduced pressure, the valve located between the first chamber and the second chamber, the pressure release means and the means for detecting the negative pressure that is applied to the wound. The connections between the housings and the other components of the apparatus are preferably air-tight or substantially air-tight. The housings may engage with the other components of the apparatus via an interference fit or barbed connections in order to simplify assembly of the apparatus and reduce manufacturing cost.

The housings may comprise a relatively soft material in the regions in which they engage the other components of the apparatus in order to facilitate the assembly of the components of the apparatus and provide good surface area contact and hence the formation of an effective seal between the components of the apparatus without the need for precision assembly. In one preferred embodiment, the housings are formed entirely of the relatively soft material. Suitable relatively soft materials include thermoplastic elastomers such as thermoplastic polyurethane or styrene-butadiene rubber.

The housings are preferably formed of a single component in order to eliminate the need for joints between multiple components that could permit the entry of gas into the chambers during the operation of the apparatus. The housing is preferably formed by a moulding process such as injection moulding. In particular, 3D printing has been found to be generally unsuitable for the formation of the housing in cases where this produces a porous structure that is not sufficiently air-tight for use with this invention.

The volume of the first and second chambers is preferably no greater than is necessary for the operation of the apparatus in order to reduce the volume of gas that must be extracted from the chambers in order to generate the desired negative pressure. In particular, the volume of the first chamber and the second chamber may be less than 5 cm$^3$, less than 3 cm$^3$, or less than 1 cm$^3$. The first and second chambers may have the same or different volumes.

The valve located between the first chamber and the second chamber may operate by substantially preventing gas flow from the first chamber into the second chamber and permitting gas flow from the second chamber into the first chamber. The valve preferably operates passively in response to changes in the negative pressure in the first chamber and the second chamber. In particular, the valve may substantially prevent gas flow from the first chamber into the second chamber when the negative pressure in the second chamber exceeds the negative pressure in the first chamber, and may permit gas flow from the second chamber into the first chamber when the negative pressure in the first chamber exceeds the negative pressure in the second chamber. The valve may permit gas flow from the second chamber into the first chamber when the negative pressure in the first chamber exceeds the negative pressure in the second chamber by less than 10 mmHg, less than 8 mmHg or less than 5 mmHg.

The valve located between the first chamber and the second chamber is preferably a one-way valve, and examples of suitable one-way valves are diaphragm valves, ball and spring valves and swing/tilt valves. One valve that is suitable for use with this invention is the SCV 67220 Barbed Check Valve by Nordson Corporation.

The pressure release means may operate by permitting the entry of gas into the first chamber. The pressure release means may communicate between the first chamber and a source of gas, such as atmospheric gas in the surroundings. The pressure release means may be a valve may prevent the entry of gas into the first chamber until the predetermined negative pressure value is reached, at which point the valve may open to permit entry of gas into the first chamber and hence prevent any further increase in negative pressure. A wide range of suitable pressure release valves are available including electronically operated valves or mechanical vales, such as ball and spring valves.

However, in one preferred embodiment, the pressure release means remains permanently open to the entry of gas into the first chamber such that the extraction of gas from the first chamber by the source of reduced pressure and the entry of gas into the first chamber via the pressure release means reach equilibrium at the predetermined negative pressure value. This form of pressure release means does not contain moving parts and hence possesses improved reliability compared with electronically operated or mechanical vales. Suitable valves of this kind include flow restrictors such as precision orifices. One precision orifice that is suitable for use with this invention is the F2815 Series Precision Orifice Of 0.004".

The means for establishing fluid communication between the second chamber and a wound may comprise a connector, such as a Luer lock or another conventional medical connector. The means preferably permits the formation of an air-tight or substantially air-tight connection between the second chamber and a wound. The means may permit connection between the second chamber and a one end of a conduit that communicates with a wound dressing for negative pressure wound therapy.

Thus, according to a second aspect of this invention, there is provided a system for negative pressure wound therapy comprising:
    an apparatus for negative pressure wound therapy according to the first aspect of this invention; and,
    a wound dressing for negative pressure wound therapy in fluid communication with the second chamber of the apparatus.

The wound dressing preferably comprises a conduit by which it is in communication with the second chamber of the apparatus. The conduit may traverses the backing layer and hence permits a negative pressure to be applied between the wound dressing and the wound by connecting the conduit to the second chamber. Suitable conduits include conventional medical tube including plastics tube formed of, for example, silicone or polyvinylchloride. The conduit is preferably transparent or at least translucent to enable blockages to be easily identified. In addition, the conduit may have an external diameter of between 4 mm and 10 mm, between 5 mm and 8 mm or about 6 mm.

The wound dressing may be any conventional wound dressing for negative pressure wound therapy and in particular may comprise a backing layer that is substantially impermeable to gas, and a skin contact layer that is able to form a seal against the skin in the regions surrounding the wound, such that a negative pressure can be established between the wound dressing and the wound. The backing layer may have a low degree of permeability to allow for the transmission of moisture vapour, and in particular may be formed of a sheet of microporous plastics material such as polyurethane. The skin contact layer preferably carries a non-adherent or low-adherence adhesive, most preferably a soft silicone gel. There are preferably perforations or gaps in the soft silicone gel in order to permit transmission of moisture vapour away from the skin and hence maintain good adhesion and a proper seal around the wound. The wound dressing may further comprise a wound packing element formed of a mass of resilient gas-permeable material such as foam, which ensures the even distribution of a negative pressure throughout the wound.

In one preferred embodiment, the wound dressing comprises an absorbent material, and preferably a superabsorbent material, that is capable of absorbing large quantities of wound exudate and hence may eliminate the need for a canister or other container for collecting excess wound exudate. "Superabsorbent material" in the context of this invention means a material that is capable of absorbing many times its own mass of water (eg up to 200, 300, 400, 500 or more times its own mass of water). Suitable superabsorbent materials include alginate, polyacrylate (ie salts of polyacrylic acid, such as sodium polyacrylate), polyacrylamide copolymers, ethylene maleic anhydride copolymer, carboxymethylcellulose, polyvinylalcohol copolymers, polyethylene oxide and starch-grafted copolymers of polyacrylonitrile. The super absorbent material may be present in particulate form, in which case the particles may be incorporated into a carrier material.

The apparatus according to the first aspect of this invention may be disposable. In particular, the apparatus may be programmed to cease functioning after a set period of time, such as 60 days, 45 days or 30 days, from the time of the first operation of the apparatus. The wound dressing may also be disposable and in particular may be replaced once the absorbent or wound packing materials become saturated with wound exudate. The lifespan of the wound dressing may therefore be significantly shorter than the lifespan of the apparatus.

Thus, according to a third aspect of this invention, there is provided a kit for negative pressure wound therapy comprising:
    an apparatus for negative pressure wound therapy according to the first aspect of this invention; and,
    a plurality of wound dressings for negative pressure wound therapy adapted for the establishment of fluid communication with the second chamber of the apparatus.

According to a fourth aspect of this invention, there is provided a method of negative pressure wound therapy comprising:
    applying a wound dressing for negative pressure wound therapy to a wound;
    establishing fluid communication between the wound dressing and the second chamber of the apparatus according to the first aspect of this invention; and,
    activating the apparatus.

BRIEF DESCRIPTION OF THE DRAWINGS

The invention will now be described in greater detail, by way of illustration only, with reference to the accompany drawings, in which.

DETAILED DESCRIPTION OF THE INVENTION

Figure 1:
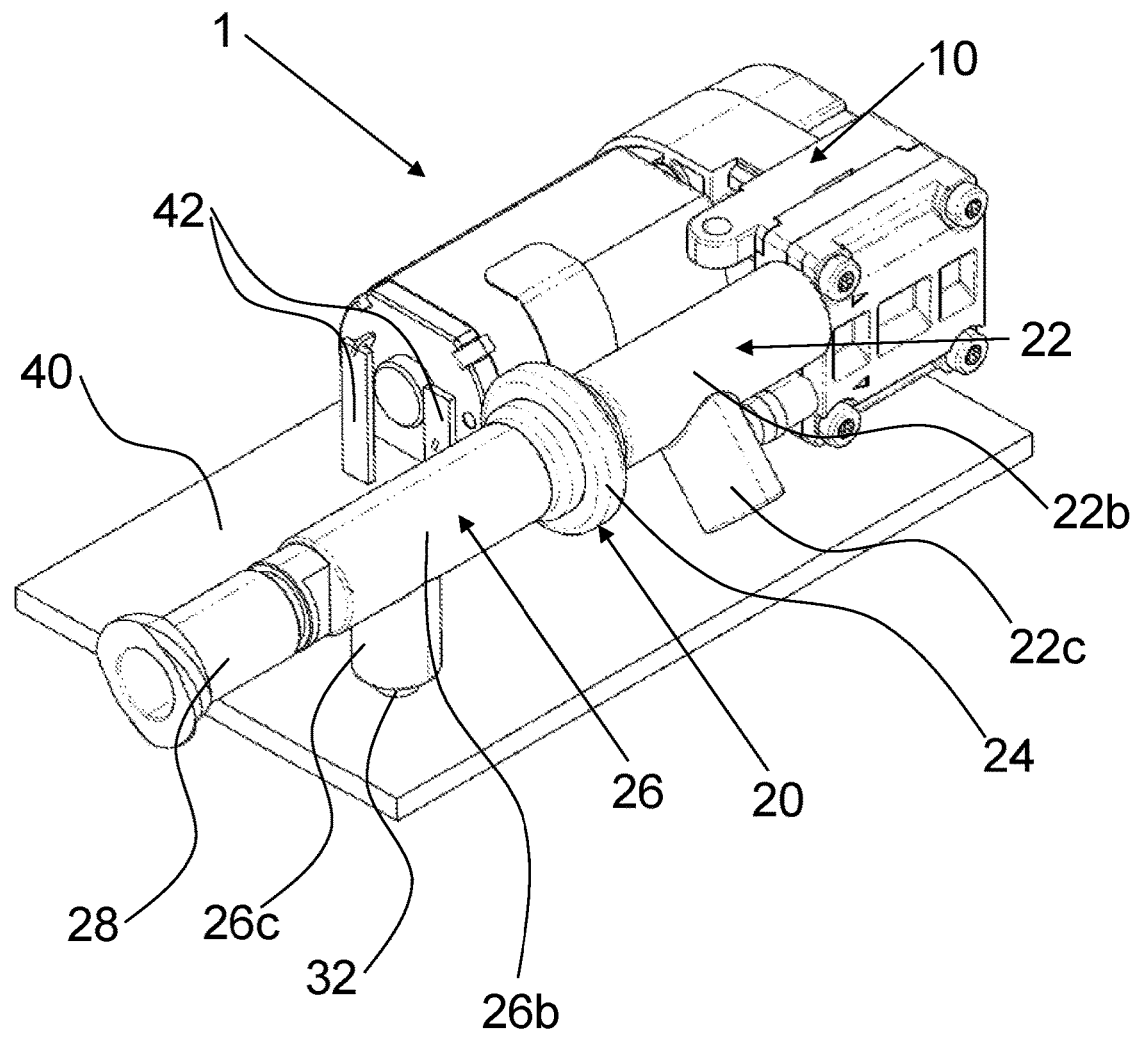
FIG. 1 is a perspective view of an exemplary embodiment of an apparatus for negative pressure wound therapy according to this invention.
Figure 2:
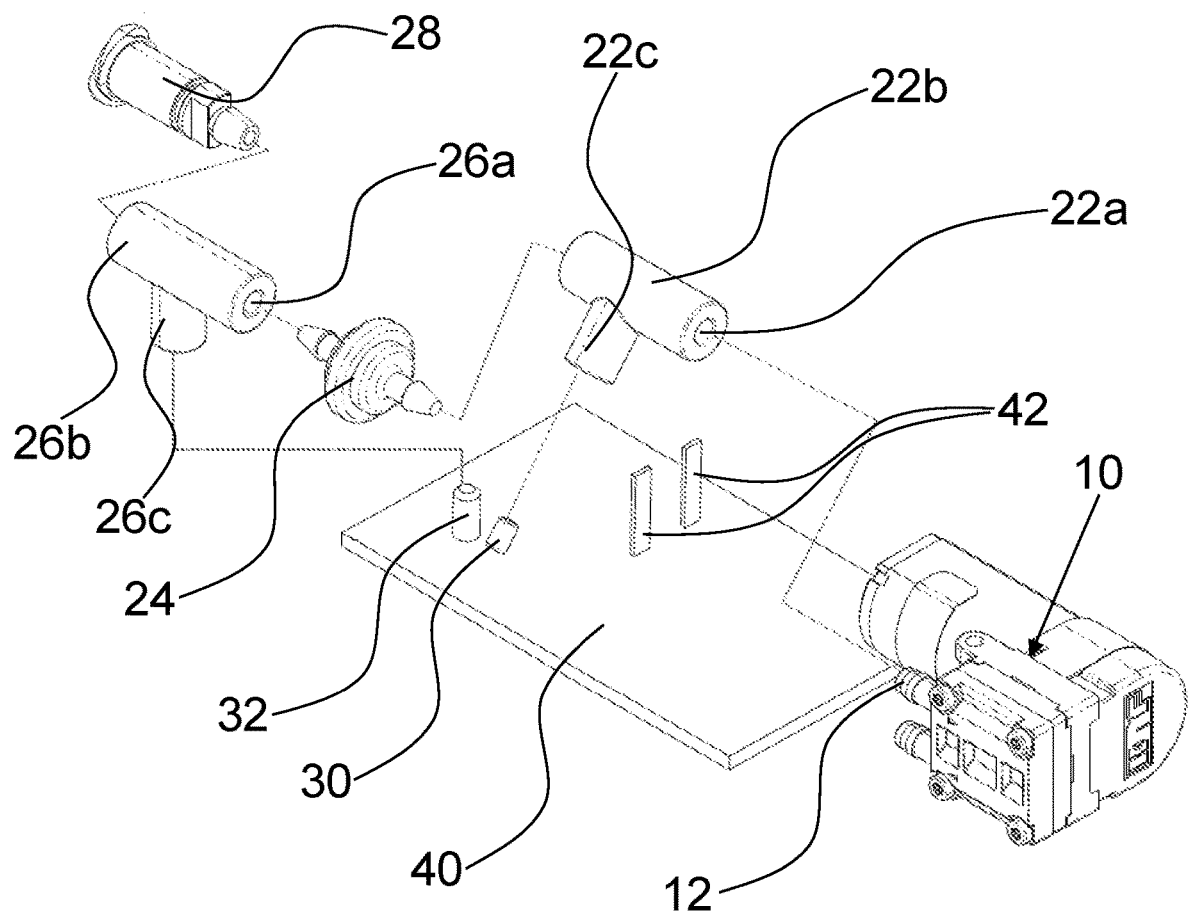
FIG. 2 is an exploded perspective view of the apparatus for negative pressure wound therapy of FIG. 1.
Figure 3:
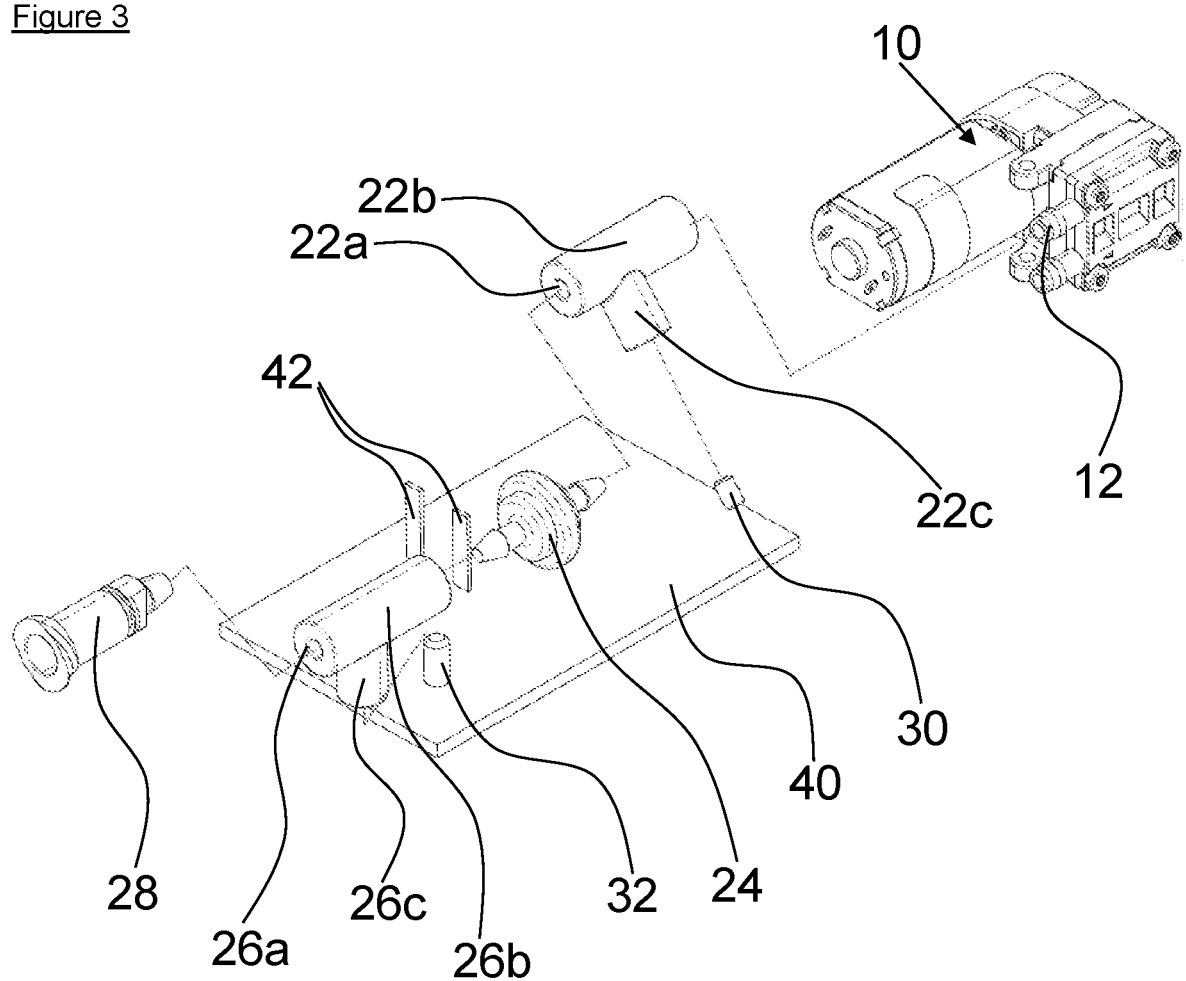
FIG. 3 is an additional exploded perspective view of the apparatus for negative pressure wound therapy of FIG. 1.

FIGS. 1 to 3 depict an exemplary embodiment of an apparatus for negative pressure wound therapy according to this invention, which is generally designated 1. The apparatus 1 comprises a source of reduced pressure in the form of a vacuum pump 10, a connector assembly 20, and a printed circuit board (PCB) 40. The PCB 40 comprises a pair of projections 42 to which the vacuum pump 10 is soldered in order to secure the vacuum pump 10 to the PCB 40. The connector assembly 20 engages with the vacuum pump 10 via a vacuum port 12 located on the vacuum pump 10.

The connector assembly 20 comprises a first tubular connector 22, a one-way valve 24, a second tubular connector 26 and a port 28. The first tubular connector 22 comprises a housing that defines a first chamber 22a, and which is formed of a primary tube 22b having an opening at each end that communicates between the first chamber 22a and the exterior of the connector 22, and a side tube 22c that branches from the primary tube 22b and has an opening at its free end that communicates between the first chamber 22a and the exterior of the connector 22. The second tubular connector 26 is of identical construction to the first tubular connector 22 and comprises a housing that defines a second chamber 26a, and which is formed of a primary tube 26b and a side tube 26c.

The first tubular connector 22 engages with the vacuum port 12 via the opening at the end of its primary tube 22b that is proximal to the vacuum pump 10, and engages with the one-way valve 24 via the opening at the end of its primary tube 22b that is distal to the vacuum pump 10. The second tubular connector 26 engages with the one-way valve 24 via the opening at the end of its primary tube 26b that is proximal to the vacuum pump 10, and engages with the port 28 via the opening at the end of its primary 26b tube that is distal to the vacuum pump 10.

The one-way valve 24 is and permits the passage of gas from the second chamber 26a into the first chamber 22a, but prevents the passage of gas from the first chamber 22a into the second chamber 26a. The port 28 is a conventional Luer lock that is capable of forming a substantially air-tight connection with a medical tube for establishing fluid communication with a wound site.

The first tubular connector 22 further comprises a pressure release valve 30 in the form of a precision orifice that is located in the opening in the free end of its side tube 22c. The pressure release valve 30 permits the entry of gas into the first chamber 22a from the surroundings in order to prevent the level by which the pressure in the first chamber 22a is reduced relative to the pressure in the surroundings (ie the "negative pressure" in the first chamber 22a) from exceeding a predetermined negative pressure value of 120 mmHg.

The second tubular connector 26 further engages with a pressure sensor 32 via the opening in the free end of its side tube 26c. The pressure sensor 32 is embedded in the PCB 40 and detects the level by which the pressure in the second chamber 26a is reduced relative to the pressure in the surroundings (ie the "negative pressure" in the second chamber 26a). The pressure sensor 32 is operably coupled to the vacuum pump 10 via the PCB 40 such that the vacuum pump 10 is deactivated when the negative pressure in the second chamber 26a reaches the desired negative pressure value.

The apparatus 1 further comprises an integral power source (not shown) for the vacuum pump 10 in the form of a battery pack and is contained within in a housing (not shown).

The tubular connectors 22,26 are formed from injection moulded thermoplastic elastomer, which is relatively soft compared with the material of the components with which they engage, namely the vacuum port 12, one-way valve 24, the port 28, the pressure release valve 30 and the pressure sensor 32. Accordingly, the tubular connectors 22,26 deform slightly in the regions that engage with the other components, ensuring good surface contact and hence a substantially air-tight connection between the components without the need for precision assembly.

In use, an occlusive dressing is applied over a wound that is to be treated. The occlusive dressing is traversed by a tube that is attached to the port 28 using a standard luer lock mechanism in order to form a substantially air-tight connection between the apparatus 1 and the wound. The vacuum pump 10 is then activated, which extracts gas from the first chamber 22a via the vacuum port 12 and the opening at the end of its primary tube 22b that is proximal to the vacuum pump 10, thus generating a negative pressure in the first chamber 22a. The pressure release valve 30 permits the entry of gas into the first chamber 22a from the surroundings, and thus prevents the negative pressure in the first chamber 22a from exceeding 120 mmHg, which is generally regarded to be the maximum negative pressure that can be safely applied to a wound.

The generation of a negative pressure in the first chamber 22a creates a pressure differential between the first chamber 22a and the second chamber 26a, resulting in the passage of gas through the one-way valve 24 from the second chamber 26a into the first chamber 22a and hence the generation of a negative pressure in the second chamber 26a. As the pressure release valve 30 prevents the negative pressure in the first chamber 22a from exceeding 120 mmHg, the negative pressure in the second chamber 26a also cannot exceed 120 mmHg. The pressure sensor 32 detects the negative pressure in the second chamber 26a and deactivates the vacuum pump 10 when the negative pressure in the second chamber 26a reaches a predetermined value. The negative pressure in the second chamber 26a at which the vacuum pump 10 is deactivated may be set electronically and may range from 80-120 mmHg.

Following deactivation of the vacuum pump 10, the negative pressure in the first chamber 22a may drop as a result of the entry of gas into the first chamber 22a through the pressure release valve 30 or the body of the vacuum pump 10. The one-way valve 24 prevents the passage of gas from the first chamber 22a into the second chamber 26a, and hence prevents the negative pressure in second chamber 26a from dropping in response to any drop in the negative pressure in the first chamber 22a.

As the second chamber 26a is in direct fluid communication with the wound via the port 28, the negative pressure in the second chamber 26a is the same as that applied to the wound. Accordingly, the negative pressure in the second chamber 26a may fluctuate due to movement of the patient or direct pressure applied to the wound, and in particular may drop as a result of the occlusive dressing not forming a complete seal around the wound.

The pressure sensor 32 detects the negative pressure in the second chamber 26a and causes activation of the vacuum pump 10 when the negative pressure in the second chamber 26a drops below a predetermined value. The negative pressure in the second chamber 26a at which the vacuum pump 10 is activated may be set electronically and may range from 80-120 mmHg and must be lower than the negative pressure at which the vacuum pump 10 is deactivated. The vacuum pump 10 continues to operate until the negative pressure in the second chamber 26a reaches the predetermined value at which the vacuum pump 10 is deactivated. The apparatus thus maintains the negative pressure that is applied to a wound at a substantially constant level for as long as is required.

The invention claimed is:

1. A disposable apparatus for negative pressure wound therapy, comprising:
   a source of reduced pressure;
   a first chamber in fluid communication with the source of reduced pressure such that the source of reduced pressure is operable to generate a negative pressure in the first chamber;
   a second chamber comprising means for establishing fluid communication with a wound;
   a one-way valve located between said first chamber and said second chamber, the one-way valve permitting the passage of gas from the second chamber into the first chamber and preventing the passage of gas from the first chamber into the second chamber;
   a pressure release means that prevents the negative pressure in the first chamber from exceeding a predetermined negative pressure value; and
   means for detecting the negative pressure that is applied to the wound; wherein:
   the source of reduced pressure is in the form of a vacuum pump occupying a volume of less than 10 cm$^3$;
   the first and second chambers are defined by housings including openings through which the first and second chambers form substantially air-tight connections with other components of the apparatus including the source of reduced pressure, the one-way valve, the pressure release means and the means for detecting the negative pressure that is applied to the wound, which air-tight connections are formed for example via interface fit or barbed connections; each of said housings being formed of a single moulded component; and
   the means for detecting the negative pressure that is applied to the wound is operably coupled to the source of reduced pressure via a programmable computer processor that permits the desired level of negative pressure that is applied to the wound to be varied; and such that the source of reduced pressure is deactivated in response to the negative pressure that is applied to the wound reaching a desired level and/or the source of reduced pressure is activated in response to the negative pressure that is applied to the wound dropping below a desired level.

2. The disposable apparatus of to claim 1, further comprising a power source for the vacuum pump.

3. The disposable apparatus of claim 1, wherein the housings comprise a relatively soft material in the regions in which they engage the other components of the apparatus.

4. The disposable apparatus of claim 3, wherein the relatively soft material is a thermoplastic elastomer.

5. The disposable apparatus of claim 1, wherein the means for detecting the negative pressure that is applied to the wound is an electronic pressure sensor.

6. The disposable apparatus of claim 5, wherein the means for detecting the negative pressure that is applied to the wound is a piezoresistive electronic pressure sensor.

7. The disposable apparatus of claim 1, wherein the vacuum pump has a maximum dimension of less than 100 mm.

8. The disposable apparatus of claim 1, wherein the vacuum pump has a maximum power consumption of less than 5 W.

9. The disposable apparatus of claim 1, wherein the volume of the first chamber is less than 5 cm$^3$ and the volume of the second chamber is less than 5 cm$^3$.

10. The disposable apparatus of claim 9, wherein the first and second chambers have different volumes.

11. The disposable apparatus of claim 9, wherein the first and second chambers have the same volume.

12. The disposable apparatus of claim 1, wherein the one-way valve located between the first and second chambers permits gas flow from the second chamber into the first chamber when the negative pressure in the first chamber exceeds the negative pressure in the second chamber by less than 10 mmHg.

13. The disposable apparatus of claim 1, wherein the one-way valve located between the first and second chambers is selected from a diaphragm valve, a ball and spring valve and a swing/tilt valve.

14. The disposable apparatus of claim 1, wherein the pressure release means permits the entry of gas into the first chamber.

15. The disposable apparatus of claim 1, wherein the pressure release means is permanently open to the entry of gas into the first chamber.

16. The disposable apparatus of claim 15, wherein the pressure release means is selected from a flow restrictor and a precision orifice.

17. The disposable apparatus of claim 1, wherein the means for establishing fluid communication between the second chamber and a wound comprises a Luer lock.

18. The disposable apparatus of claim 1, which apparatus is programmed to cease functioning after a set period of time from the time of the first operation of the apparatus.

19. A system for negative pressure wound therapy comprising:
   a disposable apparatus for negative pressure wound therapy according to claim 1; and
   a wound dressing for negative pressure wound therapy in fluid communication with the second chamber of the apparatus.

20. A kit for negative pressure wound therapy comprising:
   a disposable apparatus for negative pressure wound therapy according to claim 1; and
   a plurality of wound dressing for negative pressure wound therapy adapted for the establishment of fluid communication with the second chamber of the apparatus.

21. A method of negative pressure wound therapy comprising:
   applying a wound dressing for negative pressure wound therapy to a wound;
   establishing fluid communication between the wound dressing and the second chamber of the disposable apparatus according to claim 1; and
   activating the apparatus.

* * * * *